United States Patent
Dickson

(10) Patent No.: US 6,689,399 B1
(45) Date of Patent: Feb. 10, 2004

(54) TRANSDERMAL DELIVERY OF AN ANTI-INFLAMMATORY COMPOSITION

(76) Inventor: James R. Dickson, 4 Upper Dogwood La., Rye, NY (US) 10580

( * ) Notice: Subject to any disclaimer, the term of this patent is extended or adjusted under 35 U.S.C. 154(b) by 0 days.

(21) Appl. No.: 09/526,343

(22) Filed: Mar. 16, 2000

(51) Int. Cl.$^7$ .................................................. A61K 7/48
(52) U.S. Cl. ..................... 424/760; 514/54; 514/625; 514/627; 514/629
(58) Field of Search ................................ 424/401, 760; 514/54, 562, 627, 629, 886, 887

(56) References Cited

U.S. PATENT DOCUMENTS

| | | |
|---|---|---|
| 3,683,076 A | 8/1972 | Rovati |
| 3,697,652 A | 10/1972 | Rovati et al. |
| 4,238,505 A | 12/1980 | Engel |
| 4,313,958 A | 2/1982 | LaHann |
| 4,401,663 A | 8/1983 | Buckwalter et al. |
| 4,493,848 A | 1/1985 | LaHann et al. |
| 4,532,139 A | 7/1985 | Janusz et al. |
| 4,544,668 A | 10/1985 | Janusz et al. |
| 4,544,669 A | 10/1985 | LaHann et al. |
| 4,599,342 A | 7/1986 | LaHann |
| 4,647,453 A | 3/1987 | Meisner |
| 4,772,591 A | 9/1988 | Meisner |
| 4,801,619 A | 1/1989 | Lindblad |
| 4,812,446 A | 3/1989 | Brand |
| 4,997,853 A | 3/1991 | Bernstein |
| 5,364,845 A | 11/1994 | Henderson |
| 5,431,914 A | 7/1995 | Adekunle et al. |
| 5,665,378 A | 9/1997 | Davis et al. |
| 5,824,650 A | 10/1998 | De Lacharriere et al. |
| 5,827,886 A | 10/1998 | Hersh |
| 5,869,533 A | 2/1999 | Holt |
| 5,888,494 A | 3/1999 | Farrar et al. |
| 5,910,512 A | 6/1999 | Conant |
| 5,916,565 A * | 6/1999 | Rose et al. .................. 424/756 |
| 5,972,906 A | 10/1999 | Asculai et al. |

FOREIGN PATENT DOCUMENTS

| | | |
|---|---|---|
| EP | 0 068 590 | 1/1983 |
| EP | 0 068 592 | 1/1983 |
| EP | 0 089 710 | 9/1983 |

OTHER PUBLICATIONS

Smith, J.G., Jr. et al., "The Effects of Capsaicin on Human Skin, Liver and Epidermal Lysosome" J. Invest Dermatol. Feb. 1970; 54(2): 170–173.

Leeman, S. "Substance P" Adelman, G. et al. Encyclopedia of Neuroscience, vol. II, 1999; pp. 1968–1969.

Regoli, D. et al. "Receptors and Antagonists for Substance P and Related Peptides" Pharmacological Reviews; 1994—American Society for Pharmacology & Experimental Therapeutics, Vol 46, No. 4; pp. 551–599.

Zhang, W. Y. et al., "The Effectivenss of Topically Applied Capsaicin" Eur. J. Clin. Pharmacol. 1994; 46: 517–522.

Cordell, G. A. et al., "Capsacicin: Identification, Nomenclature, and Pharmacotherapy" The Annals of Pharmacotherapy. Mar.1993 ; 27: 330–336.

Rumsfield, J. A. et al., "Topical Capsaicin in Dermatologic and Peripheral Pain Disorders" DICP, The Annals of Pharmacotherapy. Apr.1991 ; 25: 381–387.

Holzer, P. et al., "Nociceptive Threshold After Neonatal Capsaicin Treatment" European J. Pharmacol.,1979; 58: 511–514.

Jancsó, G. et al., "Effect of Capsaicin on Morphine Analgesia–Possible Involvement of Hypothalamic Structures" Arch. Pharmacol. 1980; 311:285–288.

Yaksh, T. L., et al., "Intratecal Capsaicin Depletes Substance P in the Rat Spinal Cord and Produces Prolonged Thermal Analgesia" Science. 1979; Oct. 206: 481–483.

Duke, J.A. "CRC Handbook of Medicinal Herbs" CRC Press, Inc. 1985; 98–99; 586.

Zubrzycrka, M et al. "Substance P: Transmitter of Nociception (Minireview)", Endocrine Regulations; vol. 34, 2000, 195–201.

* cited by examiner

*Primary Examiner*—Jyothsna Venkat
(74) *Attorney, Agent, or Firm*—Proskauer Rose, LLP; Kristin H. Neuman, Esq.; James H. Shalek, Esq.

(57) ABSTRACT

The present invention provides an anti-inflammatory composition for treatment of joint and muscle pain through transdermnal delivery of a capsacinoid in conjunction with glucosamine. The ingredients of the composition of the present invention, namely, a capsacinoid in combination with a primary amine, such as glucosamine, at a high concentration, interact in a synergistic manner to provide a prolonged effect of pain relief when used in the treatment of joint and/or muscle pain associated with an inflammatory response. The prolonged pain relief effect is achieved without incurring the intense burning or stinging sensation usually associated with topical capsaicin administration. The present invention also provides methods for relieving joint and/or muscle pain associated with an inflammatory response, which employ the composition of the present invention.

19 Claims, No Drawings

TRANSDERMAL DELIVERY OF AN ANTI-INFLAMMATORY COMPOSITION

FIELD OF THE INVENTION

The present invention relates to an anti-inflammatory composition for treatment of joint and muscle pain. More specifically, the present invention provides a composition that alleviates pain associated with joint and/or muscle injuries, diseases or conditions through transdermal delivery of a casaicinoid in conjunction with a primary amine, such a glucosamine. The combination of the ingredients of the present invention, namely a capsaicinoid and a primary amine, interact in a synergistic manner to provide unexpectedly beneficial results in relief of joint and/or muscle pain associated with an inflammatory response.

BACKGROUND OF THE INVENTION

The connective tissue of mammals, such as humans, are subjected to a constant barrage of stresses and injuries throughout the life of the individual. These stresses may result from acute or chronic impacts or from the progress of various degenerative diseases, and produce painful inflammation in joint regions, such as the neck, back, arms, hips, ankles and feet. These afflictions are common, afflicting millions of Americans, and in many cases, debilitating. As a result, there is a great need for an effective and simple treatment to ease the pain associated with inflammatory connective tissue conditions.

There are a number of approaches directed to controlling the symptoms of such inflammatory connective tissue conditions. Steroids, especially corticosteroids, and non-steroidal anti-inflammatory drugs (so-called "NSAIDs"), such as aspirin (acetylsalicylic acid), ibuprofen ((2-(isobutylphenyl) propionic acid), naproxen (2-naphthaleneacetic acid, 6-methoxy-9-methyl, sodium salt), and piroxicam (4-hydroxy-2-methyl-N-2-pyridinyl-2H-1,2-benzothiazine-2-carboxamide 1,1 dioxide), are used to control the inflammation associated with connective tissue disorders. However, these drugs relieve the symptoms associated with the connective tissue disorders, but do nothing to slow the progression of the disease. Furthermore, these drugs have a number of undesirable side-effects. With respect to NSAIDS, first, NSAIDS may inhibit the body's own natural healing mechanisms, leading to further connective tissue degeneration. Second, NSAIDS also affect enzymes involved in maintaining healthy liver and kidney function, so that administration of these drugs weakens these organ systems. Finally, NSAIDS can produce gastropathy and gastric ulceration. With respect to corticosteroids, while dramatic improvements are often seen upon initial administration, corticosteroids begin to lose their effectiveness after prolonged administration. Further increases in dosage are required to overcome the loss of effectiveness, but the higher dosages themselves also eventually lose effectiveness. Furthermore, upon cessation of corticosteroid treatment, the symptoms of inflammation and swelling recur at higher levels than were experienced prior to administration. In addition, fluid retention is a serious side effect, and can lead to significant weight gain and, more importantly, dangerous levels of hypertension. Corticosteroids may also induce or contribute to osteoporosis, exacerbating what is often already a significant problem with elderly patients.

The connective tissues of mammals are capable of being regenerated by chondrocytes, cells that are responsible for the synthesis of the major components of connective tissues—collagen and proteoglycans. Collagen is a fibrous glycoprotein that is found in skin, bone, tendon, cartilage, blood vessels, and teeth. Collagen is also found in all organs, and serves as a scaffold to hold cells together. The building blocks for collagen are amino acids, and in particular the amino acids glycine, proline, hydroxyproline and hydroxylysine. Carbohydrate units are attached to collagen fibers at the hydroxylysine residues.

Proteoglycans are large, complex molecules that form the ground substance of connective tissue and determine the viscoelastic properties of joints and other structures that are subject to mechanical deformation. Proteoglycans are made up of a hyaluronic acid backbone to which are attached, at regular intervals, a core protein bearing a number of different types of modified sugars, called glycosaminoglycans. Examples of glycosaminoglycans are keratin sulfate, chondroitin sulfate, heparin, and heparin sulfate. The most important molecule in the synthesis of proteoglycans is glucosamine. Glucosamine is the precursor to the glycosaminoglycans. In addition, glucosamine forms hyaluronic acid, the backbone of proteoglycans to which the long chains of the various types of sugars are joined. Glucosamine is also a key component of synovial fluid, the liquid in joints, which provides lubrication and nutrition to cartilage.

The effects of aging and the inevitable wear and tear of daily life on structural joints mean that the structural elements of connective tissue must constantly be replaced. The rate-limiting step in the synthesis of proteoglycans is the conversion of glucose to glucosamine in the production of glycosaminoglycans. Therefore, it has been proposed to stimulate the production of proteoglycans by providing various forms of the building blocks of these complex molecules. Glucosamine administration appears to reduce the likelihood of tendon and ligament damage, as well as reducing joint inflammation, and has been shown by numerous double blind clinical trials to be both safe and effective. Administration of glucosamine appears to overcome the rate-limiting step described above by a mass action effect. U.S. Pat. No. 3,683,076, issued to Rovati et al., discloses methods for the preparation of glucosamine sulphate and glucosamine hydroiodide, useful in the treatment of degenerative joint conditions. Because these compounds oxidize readily, the compositions also preferably include a reducing agent, such as sodium hyposulfite or N-acetyl diethanolamine. U.S. Pat. No. 3,697,652, also to Rovati et al., discloses pharmaceutical preparations to treat degenerative joint conditions. Compositions contain one or more N-acyl aminocarbohydrates, preferably glucosamines and/or galactosamines. Preferably, one or more inorganic salts of alkaline earth and/or alkali metals are included (e.g., sodium sulfate, sodium iodide, etc.). U.S. Pat. No. 5,364,845, issued to Henderson, describes a therapeutic composition for the treatment and protection of connective tissue which includes glucosamine and preferably chondroitin sulfate and manganese ascorbate. U.S. Pat. No. 5,916,565, issued to Rose et al., discloses a therapeutic composition for treatment of damaged joint tissues that comprises chondroitin sulfate and glucosamine, along with multiple anti-inflammatory herbal phytochemicals, such as cayenne, which contains capsaicin.

Other components of the proteoglycans have also been provided to stimulate their production in the treatment of joint degeneration or promotion of wound healing. U.S. Pat. No. 4,801,619, issued to Lindblad, describes high molecular weight ($>3 \times 10^6$) hyaluronic acid preparations for counteracting progressive cartilage destruction. The hyaluronic acid preparations are preferably administered by intra-articular injection, and may be combined with administration of a corticosteroid or other suitable anti-inflammatory compound. U.S. Pat. No. 5,972,906, to Asculai et al., describes topically applied compositions and methods for treatment of mucous membrane disease or trauma, particularly oral mucous membrane conditions, that comprise hyaluronic acid or fragments and/or subunits thereof, along with an NSAID anti-inflammatory agent. The hyaluronic acid preparation may further include N-acetyl glucosamine or glucosamine.

Typically, glucosamine is administered by an oral route. However, oral administration of glucosamine is relatively ineffective, because the liver breaks down up to 80% of the orally administered glucosamine. Furthermore, while orally-administered glucosamine is relatively effective in reaching joint areas, many sites of pain and inflammation are poorly vascularized, and the blood-borne glucosamine has difficulty in reaching these areas. Examples of such areas are so-called "tennis elbow", "pitcher's elbow", Achilles tendonitis, pain in the tendonous areas of the back, neck, and fingers. As a result, a prolonged period of treatment is required before an beneficial effect of the drug is achieved in these sites. Glucosamine has also been administered by either a parenteral route or by intra-articular injection. While these administration methods result in an increased concentration of glucosamine in these difficult-to-reach areas, they also suffer from distinct disadvantages. For example, injections produce an increased risk of infection, and are inconvenient in comparison to oral delivery methods. In addition, parenterally-administered glucosamine still has difficulty in penetrating areas of inflammation due to the poor circulation inherent in these areas.

Capsaicin, a pungent substance derived from plants of the genus Capsicum in the Solanaceae family (e.g. hot chili peppers), is a member of a group of compounds known as capsaicinoids, which are alkaloid compounds found in high concentration in Capsicum. Capsaicinoids are responsible for the pungency, or heat, found in Capsicum. The most common capsaicinoid is capsaicin, followed by dihydrocapsaicin, nordihydrocapsaicin, homocapsaicin and homodihydrocapsaicin. Chemically, capsaicin is trans-8-methyl-N-vanillyl-6-nonenamide, dihydrocapsaicin is 8-methyl-N-vanillyl-nonanamide, nordihydrocapsaicin is 7-methyl-N-vanillyl-octamide, homocapsaicin is trans 9-methyl-N-vanillyl-7-decenamide, and homodihydrocapsaicin is 9-methyl-N-vanillyl-decamide, as shown below:

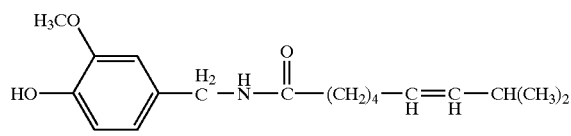

capsaicin (trans-8-methyl-N-vanillyl-6-nonenamide)

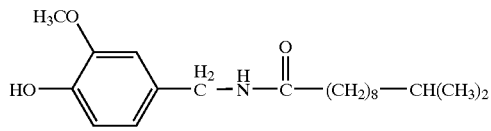

dihydrocapsaicin (8-methyl-N-vanillyl-nonanamide)

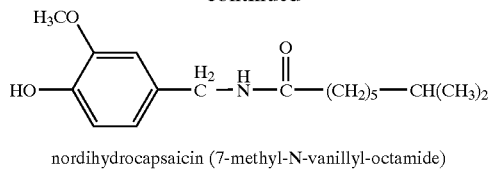

nordihydrocapsaicin (7-methyl-N-vanillyl-octamide)

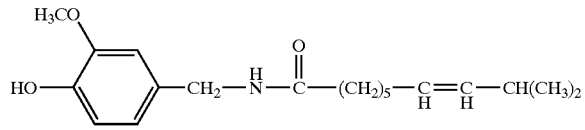

homocapsaicin (trans-9-methyl-N-vanillyl-7-decenamide)

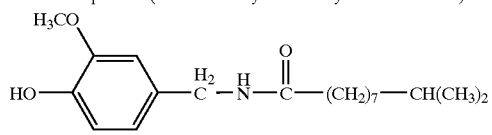

homodihydrocapsaicin (9-methyl-N-vanillyl-decamide)

Capsaicinoids are insoluble in water, but soluble in fats, oils and alcohols. In its purified form, capsaicin is a white to off-white powder, with a reported melting point of 65° C. and a boiling point at 0.01 torr of 210–220° C. Capsaicin and dihydrocapsaicin together make up between 80–90% of the capsaicinoids found in Capsicum, the other 10–20% fraction being represented by nordihydrocapsaicin (approximately 7%), homocapsaicin approximately 2%), and homodihydrocapsaicin (approximately 2%). As used herein, the terms "capsaicin" and "capsaicin-like-compounds" include all naturally occurring and synthetic capsaicinoids, as well as capsaicin analogues having physiological properties similar to those of the capsaicinoids, i.e., triggering C fiber membrane depolarization by opening cation channels permeable to calcium and sodium. These physiological effects are discussed in greater detail below.

Capsaicin produces its pungent heat effect through stimulation of excitatory afferent sensory neurons upon contact with skin or mucous membranes. There are two main phases of action. First, there is an excitation of the sensory neuron which results in the release of peptide neurotransmitters, such as substance P, calcitonin gene-related peptide (CGRP), and others, and which is responsible for the burning tingling, sensation that results when capsaicin is applied to the skin or mucous membrane. The second, slower phase is a subsequent desensitization of the nerve to stimulation. The desensitization results from the depletion of neuropeptides from the neurons, accompanied by capsaicin-mediated interference with reuptake of the neuropeptides by the neuron. This desensitization is the familiar ability of chili pepper fans to endure increasingly higher concentrations of chili pepper-containing foods through repeated exposure. It is thought that capsaicin binds to a receptor at the nerve ending of primary afferent neurons and causes release of a variety of neurotransmitter peptides, as well as subsequent blockage of the reuptake of the same neurotransmitter peptides by the afferent neurons. Substance P release is involved in transmission of pain signals from the same neurons. The depletion of substance P from the local sensory neurons, and blockage of its subsequent reuptake by capsaicin, results in the blockage of pain signals to the brain, and thereby produces an effective local anaesthetic effect.

Although detailed mechanisms of capsaicin action are not yet known, capsaicin-mediated effects are know to include the following: (i) activation of nociceptors in peripheral tissues; (ii) eventual desensitization of peripheral nociceptors to one or more stimulus modalities; (iii) cellular degeneration of sensitive A-delta and C fiber afferents; (iv) activation of neuronal proteases; (v) blockage of axonal transport; and (vi) the decrease of the absolute number of nociceptive fibers without affecting the number of non-nociceptive fibers. The effects of capsaicin have been assessed in a variety of animal studies. Capsaicin causes an increase in the rates of contraction in a variety of isolated animal tissues, including ileum smooth muscles, cardiac muscles, blood vessels, and airways. Capsaicin causes increases in both contractability and beating rate of isolated guinea pig atria. The positive inotropic (increase in contraction rate) effects of capsaicin on isolated atria are thought to be due to the release of CGRP from atrial neurons. Similarly, it is thought that the increased inotropic effects on isolated ileum are caused by substance P release.

Capsaicin selectively acts on the small diameter afferent nerve fibers (C fibers and A-delta fibers). These small diameter afferent nerve fibers are believed to be the nerves involved in pain signaling. From studies in animals, capsaicin appears to trigger C fiber membrane depolarization by opening cation channels permeable to calcium and sodium. Capsaicin is believed to bind to a receptor at the nerve ending and cause a release of a variety of neuropeptides, which results in afferent nerve conduction. Recently one of the receptors for capsaicin effects has been cloned.

Because of capsaicin's ability to desensitize nociceptors in peripheral tissues, its potential analgesic effects have been assessed in various clinical trials. Capsaicin is useful as a topical pain treatment for a wide variety of conditions, such as musculo-skeletal pain, peripheral neuropathy, post herpetic neuralgia, post-mastectomy pain, and pruritus and itching of all kinds, whether derived from contact dermatitis, insect bites, hemorrhoids, or any other source:

Synthetic capsaicin (nonyl vanillylamide, or N-vanillyl-nonanamide acts in the same manner as capsaicin, Chemically, N-vanillyl-nonanamide is as shown below:

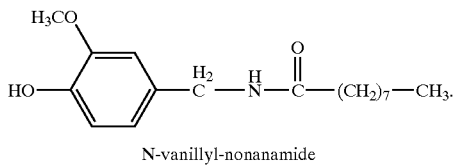

N-vanillyl-nonanamide

As mentioned above, capsaicin is believed to act on a subset of primary afferent nerves mostly of the C fiber, type (polymodal, thin, unmyelinated), although some A delta (thin, myelinated) are also capsaicin sensitive. However, the application of capsaicin itself frequently causes burning pain and hyperalgesia apart from the neuropathic pain being treated. The spontaneous burning pain and hyperalgesia are believed to be due to intense activation and temporary sensitization of the peripheral nociceptors at the site of the capsaicin application. This activation and sensitization occur prior to the desensitization phase.

The use of capsaicin or capsaicin analogs as an anaesthetic is described in U.S. Pat. Nos. 4,313,958 and 4,493,848. In addition, it is known to combine capsaicin with other analgesic compounds, such as NSAIDs (U.S. Pat. No. 4,812,446) or opioids (U.S. Pat. No. 4,599,342). The combination of these different classes of analgesic compounds produced synergistic effects, in that the combination produced greater analgesic effects than either compound alone. U.S. Pat. No. 5,431,914 describes a method for treating symptoms of pathological conditions by administering capsaicin to a specific site to treat a distal organ. The method does not rely on systemic adsorption, but takes advantage of certain nerves in the skin that lead to spinal cord segments that affect the target internal organ. U.S. Pat. No. 5,665,378 describes a transdermal therapeutic composition comprising capsaicin, a nonsteroidal anti-inflammatory drug (NSAID) and pamabrom. The NSAIDs usable in the invention include such drugs as diflunisal, fenoprofen, ibuprofen, indomethacin, meclofenamate, naproxen, and the like. The composition is preferably administered in patch form.

U.S. Pat. No. 5,869,533 discloses a delivery system for administering capsaicin along with a second ingredient that is effective to reduce the skin irritation caused by the capsaicin. The delivery system may be a patch, an aerosol, or a solid form. The second ingredient active to reduce the skin irritation caused by capsaicin is preferably either a skin anaesthetic or a compound effective to bind to the capsaicin, and is further described as one of a number of plant extracts, U.S. Pat. No. 5,910,512 discloses the use of capsaicin or a capsaicin-containing extract as a topical analgesic. A water-soluble form of capsaicin or capsaicin-containing extract is combined with hydrocolloids, magnesium oxide and disodium EDTA to form a composition that was easily applied to the skin for topical relief of pain associated with arthritis, strains, bruises and sprains. As noted above, U.S. Pat. No. 5,916,565 to Rose et al., disclosed a composition for the treatment of damaged joint tissues that comprised chondroitin sulfate and glucosamine, along with various other phytochemicals, such as the capsaicin-containing herbal cayenne.

A meta-analysis of the results of numerous clinical trials of capsaicin in promoting pain relief was prepared by Zhang and Li Wan Po (Eur J Clin Pharmacol (1994) 46:517–522). They reported results from randomized, double-blind and placebo controlled studies that evaluated the effectiveness of capsaicin in treating pain associated with diabetic neuropathy, psoriasis, osteoarthritis, postherpetic neuralgia, and postmasctectomy pain. In the case of diabetic neuropathy, they reported four trials that evaluated the use of 0.075% capsaicin cream applied four times daily for 4–8 weeks. They found that overall 73% of patients responded to capsaicin, versus 49% of patients given placebo. For osteoarthritis, three trials reported use of capsaicin cream (two using 0.025%, one using 0.075%) four times daily for four weeks. Overall, 45% of patients tested responded to capsaicin, compared to 16% treated with placebo. For postherpetic neuralgia, a single trial tested 0.075% capsaicin cream three or four times daily for three weeks. In this trial, $4/16$ (25%) of those tested reported pain relief, compared to with $1/16$ (6%) of those using only placebo. In the case of postmastectomy pain, a single trial tested 0.075% capsaicin cream applied four times daily for six weeks. In the test group, $5/13$ patients reported pain relief (38%) compared with $1/10$ (10%) of patients treated with placebo. Finally, for psoriasis, the authors reported four trials that evaluated the use of 0.025% capsaicin cream applied four times daily for 6–8 weeks. They found that overall 68% of patients responded to capsaicin, versus 42% of patients given placebo. Thus, in all the conditions examined, capsaicin showed benefits over the use of a placebo.

While capsaicin is an effective analgesic, administration of capsaicin invariably results in an initial painful burning or stinging to the skin. This painful side effect can be quite severe, and reduces patient compliance with the treatment. While repeated use of capsaicin over time periods of several weeks can cause the burning or stinging sensation to fade, a patient may choose to discontinue treatment before they can achieve beneficial levels of pain relief In addition, most capsaicin formulations require between two and four daily administrations, because the pain relief effect of the capsaicin is short-lived. Finally, the painful sensation associated with capsaicin administration may discourage extension of the use of capsaicin in the treatment of various other conditions that may be alleviated through administration of capsaicin. As noted above, others have prepared various compositions that incorporate one or more local anaesthetics to offset the painful side effects associated with topical administration of capsaicin. For example, U.S. Pat. No. 4,997,853 discloses the use of lidocaine or benzocaine to offset the painful side effects of capsaicin administration. U.S. Pat. No. 5,869,533 teaches a method for anaesthetizing against the pain caused by the topical administration of capsaicin by incorporating a second active ingredient having anaesthetic properties, and particularly various described plant extracts. However, even when these compositions were tested, not all patients experienced relief from the painful burning induced by topical capsaicin administration. Furthermore, the use of an additional anaesthetic did not reduce the requirement for repeated applications of capsaicin before the beneficial pain relief effects were obtained.

The inventor of the present application previously developed a formulation for treatment of muscle and joint pain containing capsaicin and glucosamine. In addition to capsaicin and glucosamine, that preparation also contained a number of herbal extracts, including bloodroot, blessed thistle, green tea and mint leaf that were intended to improve the palatability and anaesthetic qualities of the preparation. However, this preparation was unsatisfactory for a number of reasons. First, the preparation would separate into a number of phases within a few days, rendering it unusable. Furthermore, the preparation had an unpleasant, gritty texture. The preparation also had a dark color that was undesirable because once applied, the preparation stained clothing irreversibly. Furthermore, the preparation was not sterile, and its shelf life was only a few days. Therefore, there remains a need for an anti-inflammatory composition that is effective in treating pain and inflammation at certain sites, and which does not include the drawbacks of previous preparations. The present invention fulfills that need, and furthermore has the unexpected quality of providing an extended duration of pain relief without the intense burning or stinging feeling associated with topical administration of capsaicin-containing preparations.

SUMMARY OF THE INVENTION

The present invention provides an anti-inflammatory composition for treatment of joint and muscle pain through transdermal delivery of a capsacinoid in conjunction with a primary amine, such as glucosamine. The ingredients of the composition of the present invention, namely, a capsaicinoid in combination with glucosamine at a high concentration, interact in a synergistic manner to provide a prolonged effect of pain relief when used in the treatment of joint and/or muscle pain associated with an inflammatory response. The prolonged pain relief effect is achieved without incurring the intense burning or stinging sensation usually associated with topical capsaicin administration. The present invention also provides methods for relieving joint and/or muscle pain associated with an inflammatory response, which employ the composition of the present invention.

In one aspect of the present invention, a sterile anti-inflammatory composition is provided. The composition comprises a capsaicin, a capsaicinoid or a capsaicin analogue; a primary amine or a pharmaceutically acceptable salt thereof, and a pharmaceutically effective carrier which is effective to promote transdermal movement of at least one component of the composition upon contact with the skin of a patient with the composition. The composition is sterile, and further is substantially free of herbs or herbal preparations, which can introduce undesirable properties into the composition.

In another aspect of the present invention, a method for delivering a sterile anti-inflammatory composition to a patient comprises contacting the skin of the patient with an effective amount of a sterile anti-inflammatory composition which contains a capsaicinoid and a primary amine or a pharmaceutically acceptable salt thereof, and a pharmaceutically effective carrier which is effective to promote transdermal movement of at least one component of the composition upon contact with the skin of a patient with the composition. The composition is sterile, and further is substantially free of herbs or herbal preparations, which can introduce undesirable properties into the composition.

In another aspect of the present invention, a method for treating muscle or joint pain in a patient in need of such treatment comprises contacting the skin proximal to said muscle or joint pain with an effective amount of a sterile anti-inflammatory composition which contains a capsaicinoid and a primary amine or a pharmaceutically acceptable salt thereof, and a pharmaceutically effective carrier which is effective to promote transdermal movement of at least one component of the composition upon contact with the skin of a patient with the composition. The composition is sterile, and further is substantially free of herbs or herbal preparations, which can introduce undesirable properties into the composition.

The primary amine is preferably glucosamine or galactosamine, and should be present in an amount between about 18% and 25% by weight in the composition of the present invention. Preferably, the primary amine is glucosamine, and is present at a concentration of about 25% by weight, and more preferably, the glucosamine is present at as high a concentration as possible without causing phase separation. The capsaicinoid employed in the composition of the present invention may include one or more of trans-8-methyl-N-vanillyl-6-nonenamide (capsaicin), 8-methyl-N-vanillyl-nonanamide (dihydrocapsaicin), and N-vanillyl-nonanamide. Preferably, the capsaicinoid is trans-8-methyl-N-vanillyl-6-nonenamide (capsaicin). The composition further may include menthol, preferably at a concentration between 0.5% and 5% by weight, and more preferably at a concentration of 1% by weight.

DETAILED DESCRIPTION OF THE PREFERRED EMBODIMENTS

The present invention provides a composition that alleviates pain associated with joint and/or muscle injuries, diseases or conditions through transdermal delivery of a capsaicinoid in conjunction with a primary amine, such as glucosamine, in a pharmaceutically acceptable Use carrier. The composition is effective in the treatment of joint and/or muscle pain associated with arthritis, muscle aches, bruises, bumps and sprains. Importantly, the composition provides rapid pain relief without irritating side effects, particularly skin irritation, and the pain relief effect has a surprising prolonged duration.

The composition of the present invention contains capsaicin, a capsaicinoid or a capsaicin analogue; a primary amine such as glucosamine or a pharmaceutically acceptable salt thereof, and a pharmaceutically effective carrier, which is effective to promote transdermal movement of at least one component of the composition upon contact with the skin of a patient with the composition. The composition is sterile, and further is substantially free of herbs or herbal preparations, which can introduce undesirable properties into the composition. The composition optionally contains menthol.

The carrier is any pharmaceutically effective carrier that is effective to promote transdermal delivery of the composition of the present invention. Such carriers are well-known among those in the art. Preferably, the carrier is one of the compounds designated by the mark Pluronic™, such as Pluronic™ F-127 (BASF Corporation, Mount Olive, N.J.). The capsaicin is preferably either a natural capsaicinoid-containing extract of chili peppers, or a capsaicinoid purified from peppers or synthesized artificially. More particularly, the capsaicin may be either capsaicin trans-8-methyl-N-vanillyl-6-nonenamide), dihydrocapsaicin 8-methyl-N-vanillyl-nonanamide), the cis isomer of capsaicin cis-8-methyl-N-vanillyl-6-nonenamide), or a synthetic capsaicin., such as N-vanillyl-nonanamide or those described in U.S. Pat. No. 4,812,446 to Brand. The capsaicin may further be comprised of a combination of any of the above capsaicinoids or synthetic capsaicins. The concentration is any that is effective in producing the desired results. In general, the concentration is preferably between 0.005% by weight and 1.0% by weight. More preferably, when the capsaicinoid is capsaicin or N-vanillyl-nonanamide, the concentration preferably is between about 0.025% by weight and 0.075% by weight.

The glucosamine (2-amino-2-deoxyglucose) is preferably present at as high a concentration as possible, in order to maximize the mass action effect of the transdermally applied glucosamine. Preferably, the concentration of the glucosamine is between about 18% by weight and about 25% by weight. Most commercially available glucosamine-containing compositions contain about 4% by weight of glucosamine. If the concentration is higher than 25% by weight, the composition loses its smooth, creamy texture and instead becomes granular and gritty. Furthermore, the color of the composition changes from a light tan to a darker brown. This darker color is more noticeable than the light tan color when the composition contacts light-colored clothing. The glucosamine is preferably supplied in the form of glucosamine sulfate, but may also be supplied in the form of any other appropriate salt, such as glucosamine hydrochloride or glucosamine pentaacetate. In addition, other amines, such as galactosamine, could be substituted in place of the glucosamine.

Importantly, the composition of the present invention does not contain any additional botanicals or herbals, other than the possibility of the inclusion of capsaicin in the form of cayenne. Inclusion of such botanicals or herbals may cause the color of the composition to darken, leading to the undesirable possibility that clothing that comes into contact with the composition may be stained. In addition, it has been found by the inventor that inclusion of such additional components produces a composition having an unsatisfactory gritty texture, and also increases the possibility that the composition will separate into a plurality of physical phases.

Furthermore, the composition of the present invention is prepared in a form that is sterile. By "sterile", it is meant that the preparation is sufficiently devoid of additional bacteria, yeast, fungi, molds, etc. so that the preparation has a useful shelf life, under storage and transport conditions normal to this type of preparation, of at least one month. The preparation may be rendered of a sufficient degree of sterility by any appropriate means, including but not limited to autoclaving, irradiation, and ethylene oxide treatment. One or more of the components may be sterilized separately from the remainder of the mixture and thereafter added to the other components under sterile conditions. Alternately, the entire composition may be sterilized prior to dispensing the composition into separate tubes.

EXAMPLE

A survey was conducted to determine the effectiveness of the composition of the present invention in alleviating pain associated with a variety of inflammatory conditions. Each participant was provided with three one-ounce tubes, marked only A, B, and C. Tube A contained substrate plus 0.075% capsaicin. Tube B contained only substrate. Tube C contained substrate, 0.075% capsaicin, and 25% glucosamine. The contents of the tubes were virtually identical in color, smell and consistency. The participants were instructed to apply creams from tubes A, B or C and record their reactions according to the criteria provided. For each, the participants were instructed to apply each of the preparations into an inflamed and painful area by rubbing for several minutes, until there was a feeling of warmth. The participants were further instructed to randomly try each of the preparations until they could form an opinion as the character of each of the preparations, and not to mix the creams. The participants thereafter recorded their preparations of each of the creams according to a questionnaire supplied to them. The questions in the questionnaire were as follows:

| Question No. | Text of Question |
|---|---|
| 1 | Was the cream readily absorbed into your skin? |
| 2 | Did the cream have a pleasant aroma? |
| 3 | Did you feel any immediate sensation after applying the cream? |
| 4 | Was there any feeling of temperature change? |
| 5 | Was there a tingling feeling? |
| 6 | Was there an alteration in the pain in the affected area? |
| 7 | Was there any alteration in the swelling in the affected area? |
| 8 | If there was pain relief, was the duration of relief more than an hour? |
| 9 | Was there improved motion in the affected area? |
| 10 | Did you have the feeling that you'd like to try to increase activity level after using the product? |
| 11 | Was there any rash or other side effects associated with the cream? |

| TUBE A - Base + 0.075% Capsaicin | | | |
|---|---|---|---|
| Question No. | YES | NO | NO ANSWER |
| 1 | 59 | 0 | 8 |
| 2 | 50 | 8 | 9 |
| 3 | 58 | 0 | 9 |
| 4 | 51 | 16 | 0 |
| 5 | 49 | 18 | 0 |
| 6 | 38 | 4 | 25 |
| 7 | 0 | 0 | 67 |
| 8 | 39 | 20 | 8 |
| 9 | 25 | 5 | 37 |
| 10 | 55 | 5 | 7 |
| 11 | 0 | 58 | 9 |

| TUBE B - Base Only | | | |
|---|---|---|---|
| Question No. | YES | NO | NO ANSWER |
| 1 | 59 | 0 | 8 |
| 2 | 50 | 8 | 9 |
| 3 | 0 | 67 | 0 |
| 4 | 0 | 67 | 0 |
| 5 | 0 | 67 | 0 |
| 6 | 0 | 67 | 0 |
| 7 | 0 | 67 | 0 |
| 8 | 0 | 67 | 0 |
| 9 | 0 | 67 | 0 |
| 10 | 0 | 67 | 0 |
| 11 | 0 | 67 | 0 |

| TUBE C - Base + 0.075% Capsaicin + 25% Glucosamine | | | |
|---|---|---|---|
| Question No. | YES | NO | NO ANSWER |
| 1 | 59 | 0 | 8 |
| 2 | 50 | 8 | 9 |
| 3 | 63 | 0 | 4 |
| 4 | 60 | 2 | 5 |
| 5 | 64 | 0 | 3 |
| 6 | 65 | 1 | 1 |
| 7 | 0 | 12 | 55 |
| 8 | 61 | 1 | 5 |
| 9 | 62 | 2 | 3 |
| 10 | 50 | 8 | 9 |
| 11 | 0 | 67 | 0 |

Respondents gave identical answers for Questions 1 and 2, indicating that in all three cases (A, B and C), the creams were readily absorbed into the skin and had a pleasant aroma. Thus, the three creams were indistinguishable prior to application. Upon application of the control cream (tube B), no respondents noticed any immediate sensation, feeling of temperature change, or tingling feeling (Questions 3–5). However, while half the respondents reported that the contents of both tubes A and C produced an immediate sensation, feeling of temperature change, and tingling feeling when applied, the effects were much more noticeable when using the contents of Tube C as opposed to those of Tube A. In particular, the number of respondents reporting "NO" in questions 3–5 were 33 for Tube A, versus 2 for Tube C. The differences were even more dramatic where the different creams were evaluated for pain relief, reduction of swelling and improved range of motion (Questions 6–10). No diminution in pain or swelling, or improvement in motion in the affected area, was noticed by any respondent when using the contents of Tube B (Questions 6–9). However, almost all the respondents ($65/67$) noted a decrease in pain in the affected areas when treated with Tube C contents (Question 6), and almost all ($61/67$) reported that the duration of pain relief was greater than one hour (Question 8). In contrast, when using the contents of Tube A, only $38/67$ of the respondents reported a decrease in pain, and about the same number reported that the diminution in pain lasted longer than one hour. An even greater difference was seen in perception of improved motion (Question 9), with $62/67$ of respondents using the C cream reporting increased motion and only $25/67$ of respondents using A cream reporting increased motion. None of the respondents reported any rashes or other side effects associated with administration of any of the three preparations (Question 11).

In particular, the most surprising result was the duration of the pain relief experienced by those who employed the composition of the present invention. In only one case out of 67 did a respondent report that the effect did not last more than one hour. Many users have reported effects that last for periods exceeding 8 hours, and further that administration of the composition was not painful. This extended duration of pain relief compares favorably with the conventional pain relief medicaments containing capsaicin, which require repeated administrations, on the order of between two to four per day, to produce effective pain relief. As noted above, these repeated administrations result in an initial painful burning or stinging sensation until the patient has been using the capsaicin composition for a long enough period of time for the side-effect to fade. In contrast, the composition of the present invention requires fewer administrations to effect useful pain relief, and the painful side effects were dramatically diminished.

Without limiting the scope of the claims in any way, the inventor believes that in the immediate period after administration the feeling of heat at the site of administration of capsaicin as well as local vasoconstriction induced by capsaicin, creates the prolonged action observed in the testing of the present composition. The presence of such high concentrations of glucosamine (~25%), which upon transdermal application are far higher than are achievable with orally- or parenterally-administered glucosamine, may serve to slowly block and antagonize the effects of substance P. The glucosamine, in the concentrations employed, may not act to completely block the effect of capsaicin on the nerve fibers. Rather, the glucosamine may act competitively at the capsaicin receptor sites on the neuron. As a result, the "all or nothing" effect of capsaicin on the nerve fiber (i.e., the capsaicin either induces the release of substance P or blocks its reuptake) may be altered. In particular, at the glucosamine concentrations used in the present invention, a balance between the two opposing effects of capsaicin (i.e., the release of substance P and the desensitization effects) may be produced, leading to ongoing and simultaneous action of both effects while the substance P is slowly released from the neuron. The slower substance P release may result in local substance P concentrations sufficient to cause the feeling of heat associated with administration of the present composition, without reaching levels that would result in intense pain signals being delivered to the brain. Eventually, when the substance P depletion is completed, the anaesthetic effect of the capsaicin (i.e., blockage of substance P reuptake) may become predominant. The effect of the glucosamine is apparently due to the presence of the amine group; thus, any primary amine could theoretically be employed in the compositions employed in the present invention.

Furthermore, another end result of this effect of glucosamine on the capsaicin effect would be that the primary vasoconstrictive effect of the capsaicin is permitted to prevail for a longer time than it would in the absence of the glucosamine. In turn, the accumulated volume of the capsaicin is then sufficiently increased in the inflamed area, allowing the period of desensitization to be extended for a period of time longer than would otherwise be possible. In this fashion, the subsequent administrations of the composition of the present invention would not involve the recurring painful side effects associated with conventional capsaicin-containing formulations, and the pain relief effects associated with the present composition are extended in duration.

Various patents and publications are cited herein, and their disclosures are hereby incorporated by reference in their entireties. The present invention is not intended to be limited in scope by the specific embodiments described herein. Although the present invention has been described in detail for the purpose of illustration, various modifications of the invention as disclosed, in addition to those described herein, will become apparent to those of skill in the art from the foregoing description. Such modifications are intended to be encompassed within the scope of the present claims.

What is claimed is:

1. A composition, comprising:
   (a) a capsaicinoid;
   (b) a primary amine selected from the group consisting of glucosamine, galactosamine, and pharmaceutically acceptable salts thereof, said primary amine being present at a concentration of between about 18% and about 25% by weight; and
   (c) a pharmaceutically effective carrier, said carrier being effective to promote transdermal movement of at least one component of said composition upon contacting the skin of a patient with said composition;
   said composition further being substantially free of herbs or herbal preparations.

2. The composition of claim 1, wherein said primary amine is glucosamine or a pharmaceutically acceptable salt thereof.

3. The composition of claim 1, wherein said capsaicinoid is selected from the group consisting of capsaicin, dihydrocapsaicin, and N-vanillyl-nonanamide.

4. The composition of claim 3, wherein said capsaicinoid is capsaicin.

5. The composition of claim 1, wherein said capsaicinoid is present in a concentration between 0.005% and 1.0% by weight.

6. The composition of claim 3, wherein said capsaicinoid is capsaicin or N-vanillyl-nonanamide and is present at a concentration of between about 0.025% and 0.075% by weight.

7. The composition of claim 2, wherein said glucosamine or a pharmaceutically acceptable salt thereof is present in an amount of about 25% by weight of the composition.

8. The composition of claim 1, wherein the capsaicinoid is the cis isomer of capsaicin.

9. The composition of claim 1, wherein the capsaicinoid is capsaicin present in an amount of 0.075% by weight, and the primary amine is glucosamine present in an amount of 25% by weight.

10. A composition comprising:
    (a) a capsaicinoid;
    (b) a primary amine selected from the group consisting of glucosamine, galactosamine, and pharmaceutically acceptable salts thereof, being present at a concentration of between about 18% and about 25% by weight; and
    (c) a pharmaceutically effective carrier, said carrier being effective to promote transdermal movement of at least one component of said composition upon contacting the skin of a patient with said composition.

11. The composition of claim 10, wherein said primary amine is glucosamine or a pharmaceutically acceptable salt thereof.

12. The composition of claim 10, wherein said capsaicinoid is selected from the group consisting of capsaicin, dihydrocapsaicin, and N-vanillyl-nonanamide.

13. The composition of claim 10, wherein said capsaicinoid is capsaicin.

14. The composition of claim 10, wherein said capsaicinoid is present in a concentration between 0.005% and 1.0% by weight.

15. The composition of claim 12, wherein said capsaicinoid is capsaicin or N-vanillyl-nonanamide and is present at a concentration of between about 0.025% and 0.075% by weight.

16. The composition of claim 11, wherein said glucosamine or a pharmaceutically acceptable salt thereof is present in an amount of about 25% by weight of the composition.

17. The composition of claim 10, wherein the capsaicinoid is the cis isomer of capsaicin.

18. The composition of claim 10, wherein the capsaicinoid is capsaicin present in an amount of 0.075% by weight, and the primary amine is glucosamine present in an amount of 25% by weight.

19. A method for treating muscle or joint pain in a patient in need of such treatment, comprising rubbing into the patient's skin proximal to said muscle or joint pain the composition of claim 1 or 10.

* * * * *